United States Patent [19]

Naumann et al.

[11] 4,057,413
[45] Nov. 8, 1977

[54] METHODS AND COMPOSITIONS FOR REGULATING PLANT GROWTH USING PIPERAZINE COMPOUNDS

[75] Inventors: Klaus Naumann, Cologne; Klaus Lurssen, Grosskoenigsdorf; Klaus Sasse, Schildgen; Ulrich Holtschmidt; Gunter Schwarzmann, both of Essen, all of Germany

[73] Assignee: Bayer Aktiengesellschaft, Leverkusen, Germany

[21] Appl. No.: 612,813

[22] Filed: Sept. 12, 1975

[30] Foreign Application Priority Data

Oct. 9, 1974 Germany ............................ 2448003

[51] Int. Cl.$^2$ ............................................ A01N 9/22
[52] U.S. Cl. .......................................... 71/76; 71/92; 71/DIG. 1; 424/250; 260/268 R
[58] Field of Search ............... 71/1, 11, 27, 76, 90, 71/92; 424/250; 260/268

[56] References Cited

U.S. PATENT DOCUMENTS 3,696,106 10/1972 Ost et al. ............................ 424/250
3,736,121 5/1973 Zeeh et al. ............................ 71/76

OTHER PUBLICATIONS

Antiacetycholine Activity of Piperazine Derivatives, Light & Fanelli, Journal of Am. Pharm. Ass., 46, pp. 279–287.

*Primary Examiner*—Frank A. Spear, Jr.
*Assistant Examiner*—Ferris H. Lander
*Attorney, Agent, or Firm*—Burgess, Dinklage & Sprung

[57] ABSTRACT

Piperazine derivatives of the general formula

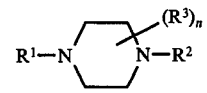

in which
R$^1$, R$^2$, and R$^3$, independently of one another, are each optionally substituted alkyl, optionally substituted alkenyl, alkynyl, cycloalkyl or aralkyl which is optionally substituted in the aryl part, and
n is 0, 1, 2, 3, or 4,
exhibit powerful plant growth-regulating properties.

44 Claims, No Drawings

METHODS AND COMPOSITIONS FOR REGULATING PLANT GROWTH USING PIPERAZINE COMPOUNDS

The present invention relates to compositions for regulating plant growth comprising certain piperazine compounds and to methods of regulating plant growth utilizing such compounds.

It is known that certain piperazine derivatives possess a therapeutic activity (see J. Amer. Pharm. Assoc. 46, 279-289 (1957) and British Patent Specification 901,187).

Further, it is known that certain 2-halogenoethyl-trialkylammonium halides possess plant growth-regulating properites from U.S. Pat. No. 3,156,554. However, the action of this compound is not always entirely satisfactory, above all if low amounts and low concentrations are used.

It has now been found that piperazine derivatives of the general formula $$R^1-N\overset{(R^3)_n}{\underset{}{\bigcirc}}N-R^2 \qquad (I)$$

in which
  $R^1$, $R^2$ and $R^3$, independently of one another, are each optionally substituted alkyl, optionally substituted alkenyl, alkynyl, cycloalkyl or aralkyl which is optionally substituted in the aryl part, and
  $n$ is 0, 1, 2, 3, or 4,
exhibit powerful plant growth-regulating properties.

Surprisingly, the piperazine derivatives according to the invention show a substantially greater plant growth-regulating action than (2-chloroethyl)-trimethylammonium chloride, known from the state of the art, which is a compound of the same type of action recognized to possess a good level of activity. The compounds which can be used according to the invention thus represent a valuable enrichment of the art.

The present invention therefore provides a plant-growth-regulating composition containing as active ingredient a compound of the formula (I) in admixture with a solid or liquefied gaseous diluent or carrier or in admixture with a liquid diluent or carrier containing a surface-active agent.

The present invention also provides a method of regulating the growth of plants which comprises applying to the plants or to a habitat thereof a compound of the formula (I), alone or in the form of a composition containing as active ingredient a compound of the formula (I) in admixture with a diluent or carrier.

The present invention further provides means of yielding crop plants the growth of which has been regulated by their being grown in areas in which immediately prior to and/or during the time of the growing a compound of the formula (I) was applied alone or in admixture with a diluent or carrier. It will be seen that the usual methods of providing a harvested crop may be improved by the present invention.

Preferably, $R^1$ is straight-chain or branched alkyl or alkenyl of up to 4 carbon atoms, each of these alkyl or alkenyl radicals being optionally substituted by hydroxyl and/or carboxyl and/or methylcarbonyl, $R^2$ is straight-chain or branched alkyl of from 6 to 18 carbon atoms, straight-chain or branched alkenyl of from 6 to 18 carbon atoms (especially with 8 to 12 carbon atoms), straight-chain or branched alkynyl of from 6 to 18 carbon atoms, cycloalkyl of from 3 to 8 carbon atoms or aralkyl of from 6 to 10 carbon atoms in the aryl part and 1 to 2 carbon atoms in the alkyl part, the aryl part being optionally substituted by halogen and/or alkyl of from 1 to 6 carbon atoms, $R^3$ is straight-chain or branched alkyl of from 1 to 6 carbon atoms, or straight-chain or branched alkenyl of from 2 to 6 carbon atoms, and $n$ is 1 or 2.

The following may be mentioned individually as examples of the active compounds which can be used according to the invention: 1-methyl-4-hexyl-piperazine, 1-methyl-4-heptyl-piperazine, 1-methyl-4-octyl-piperazine, 1-methyl-4-nonyl-piperazine, 1-methyl-4-decyl-piperazine, 1-methyl-4-undecyl-piperazine, 1-methyl-4-dodecyl-piperazine, 1-methyl-4-tridecyl-piperazine, 1-methyl-4-tetradecyl-piperazine, 1-methyl-4-pentadecyl-piperazine, 1-methyl-4-hexadecyl-piperazine 1-methyl-4-heptadecyl-piperazine, 1-methyl-4-octadecyl-piperazine, 1-methyl-4-undec-10-enyl-piperazine, 1-methyl-4-octadec-9-enyl-piperazine, 1-methyl-4-octadeca-9,12-dienyl-piperazine, 1-ethyl-4-hexyl-piperazine 1-ethyl-4-heptyl-piperazine, 1-ethyl-4-octyl-piperazine, 1-ethyl-4-nonyl-piperazine, 1-ethyl-4-decyl-piperazine, 1-ethyl-4-undecyl-piperazine, 1-ethyl-4-dodecyl-piperazine, 1-ethyl-4-tridecyl-piperazine, 1-ethyl-4-tetradecyl-piperazine, 1-ethyl-4-pentadecyl-piperazine, 1-ethyl-4-hexadecyl-piperazine, 1-ethyl-4-heptadecyl-piperazine, 1-ethyl-4-octadecyl-piperazine, 1-ethyl-4-undec-1--enyl-piperazine, 1-ethyl-4-octadec-9-enyl-piperazine, 1-methyl-4-benzyl-piperazine, 1-methyl(4-pentylbenzyl)-piperazine, 1,3-dimethyl-4-octyl-piperazine, 1,3-dimethyl-4-decyl-piperazine and 1,2,5-trimethyl-4-decyl-piperazine.

Some of the compounds which can be used according to the invention are known (see J. Amer. Pharm. Assoc. 46, 279-289 (1957) and British Pat. Specification No. 901,187). However, their use for regulating plant growth is new.

Some of the compounds which can be used according to the invention are new; however, they can be prepared in a simple manner in accordance with known processes. They are obtained, for example, when a. a piperazine of the general formula $$R^1-N\overset{}{\underset{(R^3)_n}{\bigcirc}}NH \qquad (II)$$

in which
  $R^1$, $R_3$ and n have the above-mentioned meanings, is reacted with a compound of the formula $$R^2-X \qquad (III)$$

in which
  $R^2$ has the above-mentioned meaning, and
  X is halogen or n-toluenesulfonyl, if appropriate in the presence of an inert solvent, but preferably in the absence of a solvent, at temperatures between 20° and 150° C, and the compounds of the formula (I) are liberated from the salts thus provided, by treatment with an acid-binding agent, such as, for example, aqueous alkali metal hydroxide, or when b. a piperazidide of the general formula

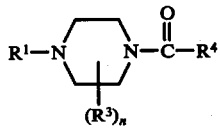

in which

R¹, R³ and n have the above-mentioned meanings, and R⁴ is optionally substituted alkyl, optionally substituted alkenyl, alkynyl or aralkyl which is optionally substituted in the aryl part is reacted with a reducing agent such as, for example, lithium alanate, in an inert solvent, such as, for example, tetrahydrofuran, at temperatures between 0° and 100° C, or when c. a nitrile of the general formula

in which

R⁴ has the above-mentioned meaning, is hydrogenated together with a divinylamine, prepared in situ, of the general formula

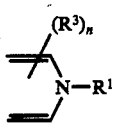

in which

R¹, R³ and n have the above-mentioned meanings, in the presence of an inert organic solvent, such as for example, dimethylformamide, and in the presence of a hydrogenation catalyst, such as, for example, Raney nickel, under a hydrogen pressure of 50 to 250 atmospheres, at temperatures between 50° C and 200° C (see British Patent Specification 901,187).

Most of the piperazine of the formula (II) which can be used as starting materials in carrying out process (a) are known (see "Handbook of Chemistry and Physics," 45th edition, page C, 479). The starting materials of the formula (II) which have not previously been described can be prepared according to known methods (see U.S. Pat. Nos. 2,525,223 and 2,636,032).

The following may be mentioned as examples of the piperazines of the formula (II): 1-methyl-piperazine, 1,2,5-trimethyl-piperazine, 1-ethyl-piperazine, 1-isopropyl-piperazine.

The compounds of the formula (III) which can be used as reactants in carrying out process (a) are also known (see Chem. Soc. 1943, 636–647; Chem. Soc. 1948, 644–654; German Patents 695,062 and 567,014; J. Amer. Chem. Soc. 55, 1978 (1933); British Pat. Specification No. 565,452 and U.S. Pat. No. 1,950,827).

The following may be mentioned as examples of compounds of the formula (III): 1-chlorohexane, 1-chloroheptane, 1-chlorooctane, 1-chlorononane, 1-chlorodecane, 1-chloroundecane, 1-chlorododecane, 1-chlorotridecane, 1-chlorotetradecane, 1-chloropentadecane, 1-chlorohexadecane, 1-chloroheptadecane, 1-chlorooctadecane, benzyl chloride and chloromethylnaphthalane as well as the corresponding bromine compounds.

In carrying out process (a), preferably 1 mole of a compound of the formula (III) is employed per mole of a piperazine of the formula (II). It is possible to use ratios above or below the stated stoichiometric ratio, but this does not produce any significant improvement in yield.

In the preparation by process (a) of the compounds usable according to the invention, the reaction products are initially obtained, after completion of the reaction, in the form of salts. To isolate the free compounds of the formula (I), the salts are covered with a water-immiscible polar organic solvent, such as, for example, ether, cyclohexanol or isobutanol, an equivalent amount of an aqueous alkali metal hydroxide solution is then added, the mixture is extracted by shaking, the organic phase is separated off and the solvent is removed.

The piperazidides of the formula (IV) which can be used as starting materials in carrying out process (b) are in part known (see U.S. Pat. No. 3,147,261). The compounds of the formula (IV) which have not previously been described in the literature can be prepared according to methods known in principle. They are obtained, for example, by reacting an acid chloride of the general formula

in which

R⁴ has the above-mentioned meaning, with a piperazine of the formula(II).

The acid chlorides of the formula (VII) are known (see Ber 17, 1378 (1884); Ber. 23, 2385 (1890); Ber. 31, 2348 (1898); Helv. Chim. Acta 22, 89 (1939); Recueil des Travaux Chimiques des Pays-Bas 18, 253 and J. Amer. chem. Soc. 66, 287 (1944)).

The nitriles of the formula (V) which can be used in carrying out process (c) are also known (see J. prakt. Chem. 1886, 634; Ber. 12, 1888 (1879); Liebigs Ann. Chem. 495, 110 (1933); Comptes Rendues 213, 270 (1941); J. Amer. Chem. Soc. 55, 348, (1933); ibid.59, 987 (1937); ibid. 64, 1362 (1942); ibid 64, 1517 (1942) ibid 66, 362 (1944) and Bl. Soc. Chim. Belg. 42, 179 (1933)).

The preparation of dinvinylamines of the formula (VI) in situ is already known (see British Pat. Specification No. 901,187).

Preparation of the active compounds is illustrated by the following preparative Examples.

EXAMPLE 1

Preparation of 1-methyl-4-dodecyl-piperazine

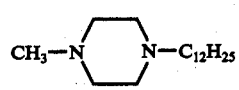

100 g (1 mole) of 1-methyl-piperazine were heated to 100° C and a total of 204.5 g (1 mole) of dodecyl chloride was added in 3 portions. After a reaction time of 15 minutes, 40 g (1 mole) of solid sodium hydroxide was added in several portions and the mixture was allowed to react for 2 hours at 140°–150° C. The reaction product was then separated from the solid inorganic residue by filtering the reaction mixture whilst hot. The inorganic residue was extracted twice with 200 ml of benzene, the benzene phase was separated off and concentrated and the residue was added to the main filtrate. The product was subjected to a fractional distillation. 177 g (66% of theory) of 1-methyl-4-dodecyl-piperazine of boiling point 90°–115° C/0.01 mm Hg were thus obtained.

EXAMPLE 2

Preparation of 1-methyl-4-decyl-piperazine

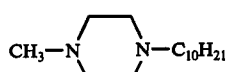
(2)

100 g (1 mole) of 1-methyl-piperazine and 176.5 g (1 mole) of decyl chloride were heated under reflux, at an external temperature of 150° C, until the reaction mixture had ceased boiling. After cooling, the solid product was extracted by shaking with a mixture with 40 g (1 mole) of sodium hydroxide in 500 ml of water and 500 ml of isobutanol. The organic phase was separated off and concentrated, and the residue was extracted with petroleum ether. After evaporating the petroleum ether solution, 180 g (75% of theory) of 1-methyl-4-decyl-piperazine were obtained in a form which was pure according to thin layer chromatography.

The IR spectrum of the reaction product showed no NH bands. The mass spectrum shows the molecular peak at m/e = 240. $n_D^{20}$ = 1.4595. Boiling point = 110°–115° C/0.1 mm Hg.

The compounds listed in Examples 3 to 7 in Table 1 which follows were obtained according to process (a) described above.

Table 1

| Ex. No. | $R^2$ | Refractive index $n_D^{20}$ | Boiling point, b.p. Melting point, m.p. |
|---|---|---|---|
| 3 | —(CH$_2$)$_7$—CH$_3$ | 1.4592 | b.p. = 110° C/0.3 mm Hg |
| 4 | —(CH$_2$)$_5$—CH$_3$ | 1.4568 | b.p. = 115° C/0.1 mm Hg |
| 5 | —(CH$_2$)$_{10}$—CH$_3$ | 1.4597 | b.p. = 115° C/0.1 mm Hg |
| 6 | —(CH$_2$)$_{12}$—CH$_3$ | — | m.p. = 20-25° C |
| 7 | —(CH$_2$)$_{16}$—CH$_3$ | — | m.p. = 58° C |

EXAMPLE 8

Preparation of 1-methyl-4-undec-10-enyl-piperazine

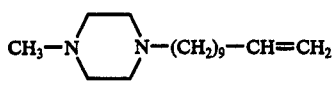
(8)

A solution of 34.6 g (0.13 mole) of undec-10-enoic acid (4-methyl)-piperazidide in 150 ml of absolute tetrahydrofuran was added dropwise to a suspension of 5.7 g (0.15 mole) of lithium alanate in 150 ml of absolute tetrahydrofuran. After completion of the addition, the reaction mixure was heated for 8 hours under reflux. For working up, the reaction mixture was allowed to cool to room temperature and 6 ml of water, 6 ml of a 15% strength aqueous sodium hydroxide solution and 18 ml of water were then successively added dropwise, whilst stirring. The precipitate which has separated out was then filtered off, the filter residue was washed with tetrahydrofuran and the filtrate was concentrated. The residue was extracted with petroleum ether. Thereafter the petroleum ether phase was separated off and the solvent was distilled off. This gave 26.2 g (80% of theory) of 1-methyl-4-undec-10-enyl-piperazine in the form of a colorless oil.

The IR spectrum of the product did not show the broad, strong amide band at 1,640 cm$^{-1}$, but a narrow, sharp band at the same wave number, which indicated the presence of an olefinic double bond. The mass spectrum showed the molecular peak at m/e = 252.

Analysis: Calculated: N = 11.1%. Found: N = 11.2%.

The purity of the isolated product could be confirmed in a simple manner by thin layer chromatography.

PREPARATION OF THE STARTING MATERIAL:

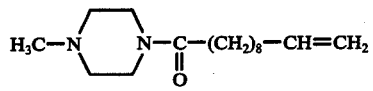

202.5 g (1 mole) of undec-10-enoic acid chloride were added dropwise to a soluttion of 110 g. (1.1 moles) of 1-methylpiperazine in 600 ml of isobutanol at 0°–10° C, whilst stirring. To convert the salt thereby produced into the free undec-10-enoic acid (4-methyl)-piperazidide, the reaction mixture was shaken at 0° C with an aqueous sodium hydroxide solution which contained 40 g (1 mole) of sodium hydroxide. The organic phase was then separated off and concentrated. After drying under a pressure of 0.1 mm Hg and at a temperature of 100° C, undec-10-enoic acid (4-methyl)-piperazidide was obtained in almost quantitative yield as a product which was pure according to thin layer chromatography.

The IR spectrum of the product shows a strong tertiary amide band at 1,640 cm$^{-1}$. $n^{20}/_d$ = 1.4882.

EXAMPLE 9

Preparation of 1-methyl-4-tetradecyl-piperzine

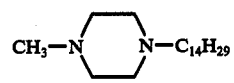
(9)

Following the procedure described in Example 8, reduction of myristic acid (4-methyl)-piperazidide gave 1-methyl-4-tetradecyl-piperazine as a product having a boiling point 140°–145°C/0.1 mm Hg. $n^{20}/_D$ = 1.4638.

The myristic acid (4-methyl)-piperazidide required as the starting material was obtained in accordance with the method indicated in Example 8, by reaction of myristic acid chloride with 1-methyl-piperazine. Melting point - 33° – 34° C.

EXAMPLE 10

Preparation of mixed 1-methyl-4-nonyl-, 1-methyl-4-decyl-, 1-methyl-4-undecyl-piperazine

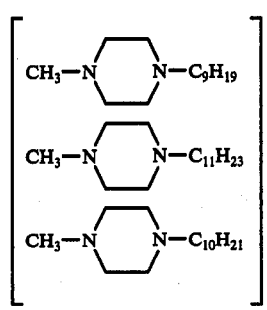
(10)

Following the process described in Example 8, reduction of "Versatic Acid 911" (4-methyl)-piperazidide gave a mixture of the piperazines of which the formulae are shown above. $n^{20}/_D = 1.4652$.

The "Versatic Acid 911" (4-methyl)-piperazidide required as the starting material was obtained in accordance with the method indicated in Example 8 by reaction of "Versatic Aciid 911" chloride with 1-methyl-piperazine. Boiling point = 125° - 135°C0.2 mm Hg.

EXAMPLE 11

Preparation of mixed 1-methyl-4-octyl-piperazine and 1-methyl-4-decyl-piperazine

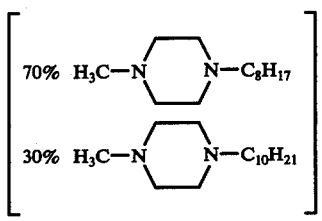
(11)

Following the process described in Example 8, reduction of coconut fatty acid (4-methyl)-piperazidide gave a mixture of the piperazines of which the formulae are shown above. Boiling point = 105° - 115°C/0.2 mm Hg. $n^{20}/_D = 1.4590$.

The coconut fatty acid (4methyl)-piperazidide mixture required as the starting material was obtained by treating the mixture obtained as first runnings on distillation of coconut fatty acids with thionyl chloride and then reacting the product isolated therefrom with 1-methyl-piperazine in accordance with the method described in Example 8.

The IR spectrum of the product, isolated in the form of an oil, showed an intense band of a tertiary amide at 1,640 cm$^{-1}$.

The active compounds which can be used according to the invention engage in the metabolism of the plants and can therefore be employed as growth regulators.

Experience to date of the mode of action of plant growth regulators has shown that an active compound can exert one or several differenct actions or plants. The actions of the compounds depend essentially on the point in time at which they are used, relative to the stage of development of the seed or of the plant, and on the amounts of active compound applied to the plants or their environment and the way in which the compounds are applied. In every case, growth regulators are intended positively to influence plants in the desired manner.

Plant growth-regulating compounds can be employed, for example, to inhibit vegetable plant growth. Such inhibition of growth is inter alia of economic interest in the case of grasses since, by repressing the growth of grass, it is possible, for example, to reduce the frequency of cutting the grass in ornamentl gardens, parks and sports grounds or at verges. The inhibition of growth of herbaceous and woody plants at verges and in the vicinity of overland pipelines or, quite generally, in areas in which heavy growth is undesired, is also of importance.

The use of growth regulators to inhibit the growth in length of cereals is also important, since by shortening the stem the danger of lodging of the plants before harvesting is reduced or completely eliminated. Furthermore, growth regulators can strengthen the stem of cereals, which again counteracts lodging.

In the case of many crop plants, inhibition of the vegetative growth permits denser planting of the crop, so that a greater yield per area of ground can be achieved. A further mechanism of increasing the yield by means of growth inhibitors is based on the fact that the nutrients benefit blossoming and fruit formation to a greater extent, whilst vegetative growth is restricted.

Propotion of vegetative growth can also frequently be achieved with growth regulators. This is of great utility if it is the vegetative parts of the plants which are harvested. Promoting the vegetative growth can, however, also simultaneously lead to a promotion of generative growth, so that, for example, more fruit, or larger fruit, is formed.

Increases in yield can in some cases also be achieved by affecting the plant metabolism, without noticeable changes in vegetative growth. Growth regulators can furthermore produce a change in the composition of the plants so as to bring about better quality of the harvested products. Thus it is possible, for example, to increase the content of sugar in sugar beet, sugar cane, pineapples and citrus fruit or to increase the protein content in soya or cereals.

Parthenocarpous fruit can be formed under the influence of growth regulators. Furthermore, the gender of the flowers can be influenced.

Using growth regulators it is also possible favorably to influence the production or the efflux of secondary plant materials. The stimulation of latex flow in rubber trees may be mentioned as an example.

During the growth of the plant, lateral branching can also be increased, by using growth regulators, through chemical breaking of the apical dominance. There is interest in this, for example, in the case of plant propagation by cuttings. However, it is also possible to inhibit the growth of side shoots, for example to prevent the formation of side shoots in tobacco plants after decapitation and thus to promote leaf growth.

The amount of leaf on plants can be controlled, under the influence of growth regulators, so that defoliation of the plants at a desired point in time is achieved. Such defoliation is of interest to facilitate mechanical harvesting, for example of grapes or cotton, or to lower the transpiration at a point in time at which the plant is to be transplanted.

Premature shedding of fruit can be prevented by the use of growth regulators. However, it is also possible to promote the shedding of fruit - for example in the case of table fruit - in the sense of a chemical thinning out, up to a certain degree. Growth regulators can also be used to reduce the force required to detach the fruit from crop plants at harvest time so as to permit mechanical harvesting of the plants or facilitate manual harvesting.

Using growth regulators it is furthermore possible to achieve an acceleration or retardation of ripening of the harvest product, before or after harvesting. This is of particular advantage since it is thereby possible to achieve optimum adaptation to market requirements. Furthermore, growth regulators can at times improve the coloration of fruit. In addition, concentration of ripening within a certain period of time is also achievable with the aid of growth regulators. This provides the preconditions for being able to carry out completely mechanical or manual harvesting in only a single pass, for example in the case of tobacco, tomatoes of coffee.

By using growth regulators it is also possible to influence the latent period of seeds or buds of plants, that is to say the endogenic annual rhythm, so that the plants, such as, for example, pineapple or decorative plants in nurseries, germinate, shoot or blossom at a time at which they normally show no readiness to do so.

Using growth regulators it is also possible to achieve a delay in the shooting of buds or the germination of seeds, for example to avoid damage by late frosts in regions where frost is a hazard.

Growth regulators can also produce halophilism in crop plants. This provides the preconditions for being able to cultivate plants on soils containing salt.

Using growth regulators, it is also possible to induce frost resistance and drought resistance in plants.

The active compounds to be used according to the present invention can be converted into the usual formulations, such as solutions, emulsions, suspensions, powders, pastes and granulates. These may be produced in known manner, for example by mixing the active compounds with extenders, that is, liquid or solid or liquefied gaseous diluents or carriers, optionally with the use of surface-active agents, that is, emulsifying agents and/or dispersing agents and/or foam-forming agents. In the case of the use of water as an extender, organic solvents can, for example, also be used as auxiliary solvents.

As liquid diluents or carriers, there are preferably used aromatic hydrocarbons, such as xylenes, toluene, benzene or alkyl naphthalenes, chlorinated aromatic or aliphatic hydrocarbons, such as chlorobenzenes, chlorothylenes or methylene chloride, aliphatic hydrocarbons, such as cyclohexane or paraffins, for example mineral oil fractions alcohols, such as butanol or glycol as well as their ethers and esters, ketones, such as acetone, methyl ethyl ketone, methyl isobutyl ketone or cyclohexanone, or strongly polar solvents, such as dimethyl formamide, dimethyl sulfoxide or acetonitrile, as well as water.

By liquefied gaseous diluents or carriers are meant liquids which would be gaseous at normal temperatures and pressures, for example aerosol propellants, such as halogenated hydrocarbons, for example freon.

As solid diluents or carriers, there are preferably used ground natural minerals, such as kaoline, clays, talc, chalk, quartz, attapulgite, montmorillonite or diatomaceous earth, or ground synthetic minerals, such as highly-dispersed silicic acid, alumina or silicates.

Preferred examples of emulsifying and foam-forming agents include non-ionic and anionic emulsifiers, such as polyoxyethylene-fatty acid esters, polyoxyethylene-fatty alcohol ethers, for example alkylarylpolyglycol ethers, alkyl sulfonates, alkyl sulfates and aryl sulfonates as well as albumin hydrolyzation products; and preferred examples of dispersing agents include lignin sulfite waste liquors and methyl cellulose.

The active compounds to be used according to the invention can be present in the formulations as a mixture with other active compounds, such as fungicides, insecticides, acaricides and herbicides, and also as a mixture with fertilizers.

The formulations in general contain from 0.1 to 95 per cent by weight of active compound, preferably from 0.5 to 90 per cent by weight.

The active compounds can be used as such, in the form of their formulations or as the use forms prepared therefrom, such as ready-to-use solutions, emulsifiable concentrates, emulsions, foams, suspensions, wettable powders, pastes, soluble powders, dusting agents and granules. They may be used in the customary manner, for example by watering, spraying, atomizing, scattering, dusting, foaming, gassing and the like. Furthermore, it is possible to apply the active compounds in accordance with the ultra-low-volume method, to spread the active-compound preparation or the active compound itself on plants or parts of plants or to inject the active-compound preparation or the active compound itself into the soil. It is also possible to treat the seeds of plants.

The active-compound concentrations can be varied within a fairly wide range. In general, concentrations of 0.00005 to 2%, preferably of 0.0001 to 0.5%, by weight are used. Furthermore, in general 0.01 to 50 kg, preferably 0.05 to 10 kg, of active compound are employed per hectare of soil surface.

The preferred period of time within which the growth regulators are applied depends on the climatic and vegetative circumstances.

The compounds according to the invention not only have very good plant-growth-regulating properties but also possess a fungicidal activity. For example, they are suitable for combating apple scab.

The examples which follow show the activity of the compounds according to the invention as growth regulators without excluding the possibility of further applications as growth regulators.

EXAMPLE A

Inhibition of growth/beans
Solvent: 10 parts by weight of methanol
Emulsifier: 2 parts by weight of polyethylene sorbitan monolaurate To prepare a suitable preparation of active compound, 1 part by weight of active compound was mixed with the stated amounts of solvent and emulsifier and the mixture was made up to the desired concentration with water.

Yound bean plants, in the stage in which the juvenile leaves have unfolded completely, were sprayed with the preparation of active compound until dripping wet. After 2 weeks, the additional growth was measured and the inhibition of growth in % of the additional growth of the control plants was calculated. 100% means that growth has stopped and 0% denotes a growth corresponding to that of the untreated control plants.

The active compounds, active compound concentrations and reslts can be seen from the table which follows:

Table A

| Active compound | Inhibition of growth/beans Active compound concentration in % | Inhibition of growth in % of the control |
|---|---|---|
| -(control) | — | 0 |
|  | 0.05 | 50 |
| 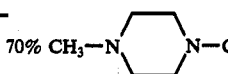 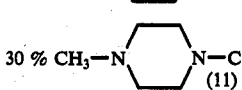 | 0.05 | 20 |

Table A-continued

| Active compound | Inhibition of growth/beans Active compound concentration in % | Inhibition of growth in % of the control |
|---|---|---|
| CH$_3$—N⌬N—C$_{11}$H$_{23}$ (5) | 0.05 | 15 |
| CH$_3$—N⌬N—C$_{17}$H$_{35}$ (7) | 0.05 | 5 |
| CH$_3$—N⌬N—C$_{13}$H$_{27}$ (6) | 0.05 | 10 |

EXAMPLE B

Inhibition of growth in chrysanthemums
 Solvent: 10 parts by weight of methanol
 Emulsifier: 2 parts by weight of polyethylene sorbitan monolaurate To prepare a suitable preparation of active compound, 1 part by weight of active compound was mixed with the stated amounts of solvent and emulsifier and the mixture was made up to the desired concentration with water.

Chrysanthemum cuttings about 10 cm high were sprayed with the preparation of active compound until dripping wet. As soon as the untreated control plants had grown to a height of about 40 cm, the additional growth was measured for all the plants and the inhibition of growth was calculated in % of the additional growth of the control plants. 100% means that growth had stopped and 0% denotes a growth corresponding to that of the untreated control plants.

The active compounds, active compound concentrations, and results can be seen from the table which follows.

Table B

| Active compound | Inhibition of growth in chrysanthemums Active compound concentration in % | Inhibition of growth in % of the control |
|---|---|---|
| - (control) | — | 0 |
| Cl—CH$_2$—CH$_2$—$\overset{\oplus}{N}$(CH$_3$)$_3$ Cl$^{\ominus}$ (known) | 0.10 | 15 |
| H$_3$C—N⌬N—C$_{12}$H$_{25}$ (1) | 0.10 | 100 |

EXAMPLE C

Inhibition of growth in soya beans
 Solvent: 10 parts by weight of methanol
 Emulsifier: 2 parts by weight of polyethylene sorbitan monolaurate To prepare a suitable preparation of active compound, 1 part by weight of active compound was mixed with the stated amounts of solvent and emulsifier and the mixture was made up to the desired concentration with water.

Young soya bean plants, in the stage in which the first adult leaves had unfolded, were sprayed with the preparation of active compound until dripping wet. After 2 weeks, the additional growth was measured and the inhibition of growth in % of the additional growth of the control plants was calculated. 100% means that growth had stopped and 0% denotes a growth corresponding to that of the untreated control plants.

The active compounds, active compound concentrations, and results can be seen from the table which follows.

Table C

| Active compound | Inhibition of growth in soya beans Active compound concentration in % | Inhibition of growth in % of the control |
|---|---|---|
| - (control) | — | 0 |
| Cl—CH$_2$—CH$_2$—$\overset{\oplus}{N}$(CH$_3$)$_3$ Cl$^{\ominus}$ (known) | 0.05 | 0 |
| CH$_3$—N⌬N—C$_{14}$H$_{29}$ (9) | 0.05 | 30 |
| CH$_3$—N⌬N—(CH$_2$)$_9$—CH=CH$_2$ (8) | 0.05 | 90 |
| [ CH$_3$—N⌬N—C$_9$H$_{19}$ ; CH$_3$—N⌬N—C$_{10}$H$_{21}$ ; CH$_3$—N⌬N—C$_{11}$H$_{23}$ ] (10) | 0.05 | 60 |

EXAMPLE D

Inhibition of growth of side shoots in tobacco
 Solvent: 10 parts by weight of methanol
 Emulsifier: 2 parts by weight of polyethylene sorbatan monolaurate To prepare a suitable preparation of active compound, 1 part by weight of active compound was mixed with the stated amounts of solvent and emulsifier and the mixture was made up to the desired concentration with water.

The shoots of tobacco plants which were about 50 cm high were pinched out. On the following day, the plants were sprayed with the preparation of active compound until dripping wet. After 3 weeks, the side shoots which had formed during this time were pinched out. The total side shoots from one treatment were weighed. The weight of the side shoots of the treated plants was compared with that of the untreated control plant. 100% inhibition denotes the absence of side shoots and 0% denotes a growth corresponding to that of the control plants.

The active compounds, active-compound concentrations, and results can be seen from the table which follows.

Table D

| Active compound | Inhibition of growth of side shoots in tobacco Active compound concentration in % | Inhibition of side shoot growth in % of the control |
|---|---|---|
| - (control) | — | 0 |
| CH$_3$—N⌬N—C$_{12}$H$_{25}$ (1) | 0.05 | 38 |
|  | 0.20 | 86 |

Table D-continued

Inhibition of growth of side shoots in tobacco

| Active compound | Active compound concentration in % | Inhibition of side shoot growth in % of the control |
|---|---|---|
| [70 % CH₃—N⟨  ⟩N—C₈H₁₇  <br>30 % CH₃—N⟨  ⟩N—C₁₀H₂₁ (11)] | 0.05<br>0.20 | 25<br>60 |
| CH₃—N⟨  ⟩N—C₁₁H₂₃ (5) | 0.05<br>0.20 | 75<br>80 |
| CH₃—N⟨  ⟩N—C₁₃H₂₇ (6) | 0.20 | 15 |

It will be understood that the foregoing specification and examples are illustrative but not limitative of the present invention inasmuch as other embodiments within the spirit and scope of the invention will suggest themselves to those skilled in the art.

What is claimed is:

1. A plant-growth-regulating composition having an agriculturally acceptable carrier and, in an amount, sufficient to exert plant-growth regulating effects, an active ingredient comprising a piperazine compound of the general formula

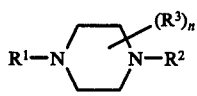

wherein
$R^1$, $R^2$, and $R^3$ are individually selected from alkyl, substituted alkyl, alkenyl, substituted alkenyl, alkynyl or cycloalkyl,
$n$ is 0, 1, 2, 3, or 4.

2. Plant-growth-regulating composition as claimed in claim 1 wherein said carrier is a solid or liquefied gaseous diluent.

3. Plant-growth-regulating composition as claimed in claim 1 wherein said carrier is a liquid diluent containing a surface-active agent.

4. Plant-growth-regulating composition as claimed in claim 1 wherein $R^1$ in the formula is alkyl of up to 4 carbon atoms.

5. Plant-growth-regulating composition as claimed 1 wherein $R^1$ is alkenyl of up to 4 carbon atoms.

6. Plant-growth-regulating composition as claimed in claim 1 wherein $R^1$ is substituted alkyl or alkenyl where the substituent is selected from the group consisting of hydroxyl, carboxyl and methylcarbonyl.

7. Plant-growth-regulating composition as claimed in claim 1 wherein $R^2$ in the formula is alkyl of 6 to 18 carbon atoms.

8. Plant-growth-regulating composition as claimed in claim 1 wherein $R^2$ in the formula is alkenyl of 6 to 18 carbon atoms.

9. Plant-growth-regulating composition as claimed in claim 1 wherein $R^2$ in the formula is alkynyl of 6 to 18 carbon atoms.

10. Plant-growth-regulating composition as claimed in claim 1 wherein $R^2$ in the formula is cycloalkyl of 3 to 8 ring carbon atoms.

11. Plant-growth-regulating composition as claimed in claim 1 wherein $R^2$ in the formula is substituted aralkyl wherein the aryl moiety is substituted with at least one member of the group consisting of halogen and alkyl of up to 6 carbon atoms.

12. Plant-growth-regulating composition as claimed in clam 1 wherein $R^3$ in the formula is alkyl of 1 to 6 carbon atoms.

13. Plant-growth-regulating composition as claimed in claim 1 wherein $R^3$ in the formula is alkenyl of 2 to 6 carbon atoms.

14. Plant-growth-regulating composition as claimed in claim 1 wherein $n$ is 0.

15. Plant-growth-regulating composition as claimed in claim 1 wherein $n$ is 1.

16. Plant-growth-regulating composition as claimed in claim 1 wherein $n$ is 2.

17. Plant-growth-regulating composition as claimed in claim 1 wherein $n$ is 3.

18. Plant-growth-regulating composition as claimed in claim 1 wherein $n$ is 4.

19. Plant-growth-regulating composition as claimed in claim 1 wherein said piperazine compound is 1-methyl-4-dodecyl-piperazine.

20. Plant-growth-regulating composition as claimed in claim 1 wherein said piperazine compound is 1-methyl-4-decyl-piperazine.

21. Plant-growth-regulating composition as claimed in claim 1 wherein said piperazine compound is 1-methyl-4-undecyl-piperazine.

22. Plant-growth-regulating composition as claimed in claim 1 wherein said piperazine compound is 1-methyl-4-undec-10-enyl-piperazine.

23. Method of inhibiting growth of plants which method comprises applying to the plants of their habitat effective amounts of a piperazine compound of the formula

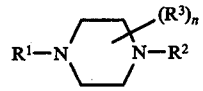

herein
$R^1$, $R^2$, and $R^3$ are individually selected from alkyl, substituted alkyl, alkenyl, substituted alkenyl, alkynyl, cycloalkyl, aralkyl or substituted aralkyl substituted in the aryl part, and
$n$ is 0, 1, 2, 3, or 4.

24. Method as claimed in claim 23 wherein $R^1$ in the formula is alkyl of up to 4 carbon atoms.

25. Method as claimed in claim 23 wherein $R^1$ is alkenyl of up to 4 carbon atoms.

26. Method as claimed in claim 23 wherein $R^1$ is substituted alkyl or alkenyl where the substituent is selected from the group consisting of hydroxyl, carboxyl and methylcarbonyl.

27. Method as claimed in claim 23 wherein $R^2$ in the formula is alkyl of 6 to 18 carbon atoms.

28. Method as claimed in claim 23 wherein $R^2$ in the formula is alkenyl of 6 to 18 carbon atoms.

29. Method as claimed in claim 23 wherein $R^2$ in the formula is alkynyl of 6 to 18 carbon atoms.

30. Method as claimed in claim 23 wherein $R^2$ in the formula is cycloalkyl of 3 to 8 ring carbon atoms.

31. Method as claimed in claim 23 wherein $R^2$ in the formula is aralkyl of 6 to 10 carbon atoms in the aryl part and 1 to 2 carbon atoms in the alkyl part.

32. Method as claimed in claim 23 wherein $R^2$ in the formula is substituted aralkyl wherein the aryl moiety is substituted with at least one member of the group consisting of halogen and alkyl of up to 6 carbon atoms.

33. Method as claimed in claim 23 wherein $R^3$ in the formula is alkyl of 1 to 6 carbon atoms.

34. Method as claimed in claim 23 wherein $R^3$ in the formula is alkenyl of 2 to 6 carbon atoms.

35. Method as claimed in claim 23 wherein $n$ in the formula is 0.

36. Method as claimed in claim 23 wherein $n$ in the formula is 1.

37. Method as claimed in claim 23 wherein $n$ in the formula is 2.

38. Method as claimed in claim 23 wherein $n$ in the formula is 3.

39. Method as claimed in claim 23 wherein $n$ in the formula is 4.

40. Method as claimed in claim 23 wherein said piperazine compound is 1-methyl-4-dodecyl-piperazine.

41. Method as claimed in claim 23 wherein said piperazine compound is 1-methyl-4-decyl-piperazine.

42. Method as claimed in claim 23 wherein said piprazine compound is 1-methyl-4-undecyl-piperazine.

43. Method as claimed in claim 23 wherein said piperazine compound is 1-methyl-4-undec-10-enyl-piperazine.

44. Plant growth regulating composition as claimed in claim 1 wherein the agriculturally acceptable carrier is a liquid carrier containing a surface-active agent or a solid pulverulent carrier.

* * * * *

UNITED STATES PATENT AND TRADEMARK OFFICE
CERTIFICATE OF CORRECTION

PATENT NO. : 4,057,413
DATED : November 8, 1977
INVENTOR(S) : Naumann et al

It is certified that error appears in the above-identified patent and that said Letters Patent are hereby corrected as shown below:

Title Page, Inventors, "Lurssen" should be -- Lürssen --,
"Gunter" should be -- Günter --.

Column 1, line 16, "properites" should be -- properties --.

Column 2, line 31, "1--" should be -- 10- --.

Column 3, line 63, "naphthalane" should be -- naphthalene --.

Column 6, line 35, "piperzine" should be -- piperazine --.

Column 7, line 8, "Aciid" should be -- Acid --.

Column 7, line 30, "(4methyl)" should be -- (4-methyl) --.

Column 7, line 59, "ornamentl" should be -- ornamental --.

Column 8, line 10, "Propotion" should be -- Promotion --.

Column 9, line 31-32, "chlorothylenes" should be
-- chloroethylenes --.

Column 10, line 51, "reslts" should be -- results --.

Signed and Sealed this

Fourth Day of April 1978

[SEAL]

Attest:

RUTH C. MASON
Attesting Officer

LUTRELLE F. PARKER
Acting Commissioner of Patents and Trademarks